United States Patent [19]
Clerici et al.

[11] Patent Number: 5,571,762
[45] Date of Patent: Nov. 5, 1996

[54] CATALYST AND PROCESS FOR THE ALKYLATION OF ALIPHATIC HYDROCARBONS WITH OLEFINS

[75] Inventors: Mario G. Clerici, San Donato Milanese; Carlo Perego, Carnate; Alberto de Angelis, Legnano; Luciano Montanari, Brescia, all of Italy

[73] Assignees: Eniricerche S.p.A., Milan; AGIP Petroli S.p.A., Rome, both of Italy

[21] Appl. No.: 283,509

[22] Filed: Aug. 1, 1994

[30] Foreign Application Priority Data

Aug. 6, 1993 [IT] Italy ............................ MI93A1796

[51] Int. Cl.$^6$ ............................ B01J 31/26; B01J 27/02; B01J 21/08
[52] U.S. Cl. ............................ 502/155; 502/216; 502/232; 585/709
[58] Field of Search ............................ 502/155, 216, 502/232

[56] References Cited

U.S. PATENT DOCUMENTS

| | | | |
|---|---|---|---|
| 4,547,474 | 10/1985 | Olah | 502/168 |
| 4,847,223 | 7/1989 | Le Van Mao et al. | 502/62 |
| 5,179,052 | 1/1993 | Knifton | 502/62 |
| 5,288,685 | 2/1994 | Kallenbach et al. | 502/168 |

FOREIGN PATENT DOCUMENTS

| | | |
|---|---|---|
| 0352856 | 1/1990 | European Pat. Off. . |
| 0433954A1 | 6/1991 | European Pat. Off. . |
| 0539277A1 | 4/1993 | European Pat. Off. . |

*Primary Examiner*—Ponnathapura Achutamurthy
*Attorney, Agent, or Firm*—Oblon, Spivak, McClelland, Maier & Neustadt, P.C.

[57] ABSTRACT

A process for the alkylation of aliphatic hydrocarbons with olefins catalyzed by a silica-based material, characterised in that the surface Si—OH groups of said silica are esterified with a fluoroalkylsulphonic acid of formula $CF_3(CF_2)_nSO_3H$, where n is a whole number between 0 and 11, said material having a Hammett acidity $Ho \leq -11.4$.

18 Claims, No Drawings

CATALYST AND PROCESS FOR THE ALKYLATION OF ALIPHATIC HYDROCARBONS WITH OLEFINS

This invention relates to the alkylation of aliphatic hydrocarbons in the presence of an acid catalyst, and to the catalyst itself. The acid-catalyzed alkylation of aliphatic hydrocarbons with olefins is a well known process in the preparation of high-octane products to be added to gasolines for improving their characteristics.

This reaction can be conducted using strong mineral acids, in particular concentrated sulphuric acid or anhydrous hydrofluoric acid, as catalyst.

This acids are used in excess over the feed mixture and result in the formation of oligomers and a large quantity of fluorinated and sulphonated by-products. In addition, hydrofluoric acid is a low-boiling liquid (B.P.=19° C.) which in the case of accidental escape from the reactor can form extremely corrosive acid clouds difficult to eliminate. Sulphuric acid, which requires a reaction temperature of less than 10° C. to maintain a sufficiently high product quality, forms high viscosity emulsions which are difficult to mix, and also results in the formation of large quantities of sulphonated compounds which involve costly disposal. To avoid the aforesaid problems it has been sought to use solid catalysts. In particular, U.S. Pat. Nos. 3,851,004, 4,384,161, 3,647,916 and 5,073,665 describe the use of Y and X zeolites exchanged with salts of metals pertaining to the lanthanum group. These catalysts do not exhibit a sufficiently high productivity, in terms of quantity of the alkylated product, to make their industrial application interesting. To this must be added the short duration of the catalytic cycle and a reduction in catalyst properties during successive regeneration operations. FR 2631956 describes the use of beta zeolite in acid form as an alkylation catalyst. Again in this case the results achieved do not seem to be promising for its use at an industrial level. Catalyst systems based on Lewis acids, mainly $AlCl_3$ and $BF_3$, supported on inert oxides have also been proposed (U.S. Pat. Nos. 4,918,255, 4,384,161, WO 900053, WO 900054, U.S. Pat. Nos. 3,855, 343, 4,935,577 and 5,012,039). The best results seem to be obtained with boron trifluoride with added traces of water, but problems remain regarding the system stability under the working conditions, due mainly to active phase loss.

It is also known to use trifluoromethanesulphonic acid as a catalyst for hydrocarbon alkylation with olefins. U.S. Pat. Nos. 3,970,721, 4,118,433, GB 1463320 and CA 1020590 describe the use of this acid as an additive for sulphuric acid or hydrofluoric acid to improve their catalytic properties. The improvement in the results obtained does not appear to be sufficient to compensate the increased costs resulting from the use of this costly reagent. EP 433954 describes a process for hydrocarbon alkylation with olefins which uses triflic acid adsorbed on previously dried silica as catalyst. This system enables an alkylate of sufficient quality to be obtained, but the catalyst has a rather low stability with time due to elution phenomena. In addition, the presence of free triflic acid can easily result in corrosion phenomena.

We have now found a catalyst for hydrocarbon alkylation with olefins which not only exhibits excellent catalytic performance, exceeding that achievable using triflic acid adsorbed on silica, but also possesses considerable stability with time, and can be easily regenerated.

The present invention therefore provides a silica-based material characterised in that the surface Si—OH groups of said silica are esterified with a fluoroalkylsulphonic acid of formula $CF_3(CF_2)_nSO_3H$, where n is a whole number between 0 and 11, said material having a Hammett acidity $Ho \leq -11.4$.

Materials with a Hammett acidity Ho <−12 constitute a preferred aspect of the present invention.

Presumably the material of the present invention carries on the silica surface substituents of formula (I)

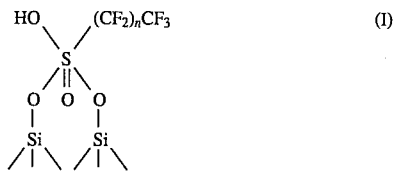

In accordance therewith, on $^{29}Si$—MAS—NMR analysis a signal is observed at about −110 ppm (TMS reference) characteristic of bulk silicon $Si$—$(OSi)_4$, and at about −103 ppm attributable both to silicon with a hydroxyl substituent, Si—OH, and to silicon bound to an —O—S substituent, Si—O—S. The evidence for the presence of two species in the signal at −103 ppm was provided using the $^{29}Si$—MAS—NMR method in cross-polarization (CP), which highlights the NMR signal of those silicons spatially close to hydrogen (Si—OH type). In this respect, comparing the $^{29}Si$—CP—MAS—NMR spectra of the materials of the present invention with the silica precursor, a significant decrease in the presence of Si—OH species was noted in the spectra of the new materials, whereas the NMR non-CP signal at —103 ppm does not decrease. This is in accordance with the formation of a chemical bond between the silica and the fluoroalkylsulphonic acid, which reduces the surface Si—OH species (found in CP), to form silicon-oxygen-sulphur Si—O—S species (not found in CP).

In addition, the material of the present invention shows an IR signal at 1546 $cm^{-1}$ after treatment with pyridine. This signal, attributable to the interaction of pyridine with a Bronsted site, is in accordance with the presence of the acid OH group in formula (I). Materials with a Hammett acidity Ho of between −11.4 and −12 also provide good catalytic performance.

Preferably the fluoroalkylsulphonic acid which esterifies the surface Si—OH groups of the silica is of formula $CF_3(CF_2)_nSO_3H$, where n is a whole number between 0 and 5.

Even more preferably trifluoromethanesulphonic acid (triflic acid) $CF_3SO_3H$ is used.

In this particular case it is presumable that the following substituents are present on the silica surface:

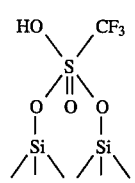

According to a preferred aspect, this material has a Hammett acidity of between −13.5 and −14.

The present invention also provides the method for preparing the aforedescribed new materials. Said method consists of:

a) mixing together tetraethylsilicate and fluoroalkylsulphonic acid of formula $CF_3(CF_2)_nSO_3H$, where n is a whole number between 0 and 11, in aqueous solution in a $CF_3(CF_2)_nSO_3H/Si(OEt)_4$ weight ratio of between 0.1 and 30%, to obtain a gel;

b) drying the gel obtained;

c) reacting the dried gel with thionyl chloride in a $SOCl_2$/gel weight ratio of between 100 and 1;

d) removing the excess thionyl chloride by distillation.

Stage a) consisting of hydrolysis of the tetraethylsilicate by the fluoroalkylsulphonic acid is conducted at a temperature between ambient and 100° C. The preferred procedure is to dilute the fluoroalkylsulphonic acid in distilled water heated to the chosen temperature and then add the tetraethylsilicate.

The fluoroalkylsulphonic acid used is preferably of formula $CF_3(CF_2)_nSO_3H$, where n is a whole number between 0 and 5. Even more preferably trifluoro-methanesulphonic acid (triflic acid) $CF_3SO_3H$ is used. The time for complete gelling varies depending on the temperature and on the concentrations, and is normally within the range of 0.5–24 hours.

Conveniently, in the reaction mixture the $CF_3(CF_2)_nSO_3H/Si(OEt)_4$ weight ratio is chosen within the range of 5–20%. The gel formed following hydrolysis is dried in stage b) under vacuum at a temperature of between 20° and 80° C., preferably 50°–60° C., for 12–48 hours.

The dried gel is subjected in stage c) to dehydration with thionyl chloride. The reaction is conducted at a temperature of between 20° and 50° C. for 4–12 hours. The thionyl chloride is then removed by distilling it off under vacuum, preferably at ambient temperature.

The catalyst of the present invention can also be conveniently prepared by a process of thermal type. This process, which represents a further aspect of the present invention, consists of thermally treating anhydrous silica and fluoroalkylsulphonic acid $CF_3(CF_2)_nSO_3H$, where n is between 0 and 11, in a $CF_3(CF_2)_nSO_3H/SiO_2$ weight ratio of between 0.1 and 30%, and preferably between 5 and 20%, at a temperature of between 50° and 300° C., preferably between 100° and 200° C., for 12–48 hours. It is convenient to operate at a temperature close to the boiling point of the acid. The anhydrous silica is prepared by drying at a temperature of about 400° C. for 12–48 hours. The fluoroalkylsulphonic acid used is preferably of formula $CF_3(CF_2)_nSO_3H$, where n is a whole number between 0 and 5. Even more preferably trifluoromethanesulphonic acid is used.

According to a further synthesis method, which facilitates the obtaining of a catalyst according to the present invention with uniform distribution of the active phase, fluoroalkylsulphonic acid $CF_3(CF_2)_nSO_3H$ is dissolved in a solvent, mixed with anhydrous silica in a $CF_3(CF_2)_nSO_3H/SiO_2$ weight ratio of between 0.1 and 30%, the solvent is then removed by stripping, possibly under vacuum, and the system subjected to thermal treatment at a temperature of between 50° and 300° C. for 12–48 hours.

Solvents suitable for this purpose are those solvents inert towards both fluoroalkylsulphonic acid and silica which have a boiling point lower than that of fluoroalkylsulphonic acid so that they can be easily removed by stripping, possibly under hot conditions.

Suitable solvents include for example water, freons, trifluoroacetic acid and trifluoroacetic anhydride. The freon 1,1,2-trichloro-2,2,1-trifluoroethane is preferably used.

The catalyst of the present invention is active in the alkylation of aliphatic hydrocarbons with olefins, it exhibits superior performance than triflic acid adsorbed on silica, it is very stable with time under the reaction conditions, and is easily regenerated.

A further aspect of the present invention is therefore a process for the alkylation of aliphatic hydrocarbons with olefins in the presence of a silica-based catalyst, characterised in that the surface Si—OH groups of said silica are esterified with a fluoroalkylsulphonic acid of formula $CF_3(CF_2)_nSO_3H$, where n is a whole number between 0 and 11, said material having a Hammett acidity $Ho \leq -11.4$.

The use of materials with a Hammett acidity $Ho < -12$ constitutes a preferred aspect of the present invention.

Preferably the fluoroalkylsulphonic acid used to esterify the surface Si—OH groups of the silica is of formula $CF_3(CF_2)_nSO_3H$, where n is a whole number between 0 and 5.

Even more preferably trifluoromethanesulphonic acid (triflic acid) $CF_3SO_3H$ is used.

This process consists of alkylating an aliphatic hydrocarbon substrate with an alkylating agent of olefinic type by passing the mixture of hydrocarbon and olefin under alkylation conditions through a reactor with a fixed catalyst bed.

The alkylation reaction is conducted at a temperature of between −20° and 100° C. at a pressure of between 5 and 40 atm and an LHSV space velocity of between 0.1 and 10 $h^{-1}$. The operating temperature is conveniently close to ambient, with a space velocity of between 2 and 4 $h^{-1}$, and preferably between 2 and 3 $h^{-1}$.

The hydrocarbon substrate consists of a $C_4$–$C_{10}$ isoalkane. The substrate is preferably isobutane.

The alkylating agent is a $C_2$–$C_{10}$ olefin. The olefin is preferably 1-butene, 2-butene or their mixtures.

The weight ratio of hydrocarbon substrate to alkylating agent in the mixture fed to the reactor is between 5:1 and 100:1.

The products obtained with this process are mainly trimethyl pentanes (TMP), of which the product present in greatest concentration is 2,2,4-trimethylpentane (isooctane).

The catalyst of the present invention can be easily regenerated after removal from the reaction environment, by operating in the following manner:
1) washing the catalyst with water, resulting in hydrolysis of the bonds between the silica and fluoroalkylsulphonic acid and extraction of the fluoroalkylsulphonic acid into the aqueous phase,
2) regenerating the silica by thermal treatment in air at 400°–700° C.,
3) recovering the fluoroalkylsulphonic acid from the aqueous phase by distillation and subsequent drying, then reacting it with the regenerated silica at a temperature of between 50° and 300° C., preferably 100°–200° C., for 12–48 hours.

The following examples are given to illustrate the present invention.

EXAMPLE 1

Catalyst preparation 72 ml of distilled water are placed in a beaker and heated to 60° C., after which 3 ml of triflic acid are added while agitating. 42 g of tetraethylorthosilicate are added while maintaining this temperature. Complete gelling is achieved after about 2 hours, the gel obtained is dried at 50° C. for 24 hours and is then reacted with 50 ml of thionyl chloride for 5 hours at 25° C.. On termination the excess thionyl chloride is distilled off under vacuum at ambient temperature.

A catalyst is obtained having a surface area of 560 $m^2/g$. By $^{29}Si$ NMR analysis and the cross-polarization technique it is found that in the product obtained the Si—OH groups initially present on the silica surface have decreased to 66% of their initial value, whereas a new species Si—O—S (34%) has formed.

EXAMPLE 2

Catalyst preparation 11 cc of 70–230 mesh silica previously dried for 24 hours at 400° C. are placed in a 14 ml pyrex glass vial. 1 ml of triflic acid is then dripped in, the vial is sealed and is maintained at 150° C. for 48 hours. A catalyst is obtained having a surface area of 500 $m^2/g$. Using $^{29}Si$ NMR analysis and the cross-polarization technique it is found that in the product obtained the Si—OH groups initially present on the silica surface have decreased to 68% of their initial value, whereas a new species Si—O—S (32%) has formed.

EXAMPLE 3

Catalyst preparation 50 ml of a solution consisting of 2 ml of triflic acid in 48 ml of anhydrous 1,1,2-trichloro-2,2,1-trifluoroethane are placed in a previously flame-heated flask under nitrogen, and 20 ml of 70–100 mesh silica previously treated at 400° C. for 24 hours are added to this solution.

The system is kept under agitation for 30 min, after which the solvent is stripped off under vacuum for 3 h. After this time period the total disappearance of the NMR signal attributable to the fluorine present in the freon molecule is noted in the solid residue.

The solid consisting of silica and triflic acid is then placed in a glass vial which is sealed and maintained at 165° C. for 24 h.

EXAMPLE 4

Catalyst preparation

A solution consisting of 50 ml of trifluoroacetic acid and 2 ml of triflic acid are placed in a previously flame-heated 100 ml flask, and 20 ml of silica previously treated at 400° C. for 24 hours are added.

The solution is then agitated for 30 min, after which the trifluoroacetic acid is distilled off under vacuum at 70° C. for 5 h.

An acidimetric titration is then conducted on the residual solid, the acidity concentration found being equal to 100% of the triflic acid content.

The solid consisting of silica and triflic acid is then placed in a glass vial which is sealed and maintained at 165° C. for 24 h.

EXAMPLE 5

Catalyst preparation

A solution consisting of 10 ml of distilled water and 2 ml of triflic acid is placed in a 100 ml flask, and 10 ml of 70–100 mesh silica are added.

The suspension is dried under vacuum at a temperature of 100° C. for 12 hours.

After this time period a product of $H_o=-11.4$ is obtained.

EXAMPLE 6

11 cc of catalyst prepared in accordance with Example 1 are placed in a reactor of diameter 0.76 cm and length 26 cm.

A mixture containing isobutane as substrate and 1-butene as alkylating agent in an isobutane: 1-butene ratio of 20:1 is fed to the reactor at a temperature of 25° C., a pressure of 17 bar and a flow rate of 0.9 ml/min. The results obtained are shown in the following table:

| $C_8$ yield % molar | Conversion | TMP % | Time (min) |
| --- | --- | --- | --- |
| 80 | 99 | 76 | 20 |
| 94 | 99 | 76 | 60 |
| 99 | 99 | 76 | 360 |

TMP% indicates the trimethylpentane selectivity.
Triflic acid does not appear in the effluent.

EXAMPLE 7

11 cc of catalyst prepared in accordance with Example 2 are placed in a reactor of diameter 0.76 cm and length 26 cm.

A mixture containing isobutane as substrate and 1-butene as alkylating agent in an isobutane: 1-butene ratio of 20:1 is fed to the reactor at a temperature of 25° C., a pressure of 17 bar and a flow rate of 0.9 ml/min. The results obtained are shown in the following table:

| $C_8$ yield % molar | Conversion | TMP % | Time (hours) |
| --- | --- | --- | --- |
| 99 | 99 | 68 | 1 |
| 95 | 99 | 68 | 3 |
| 79 | 99 | 69 | 24 |

TMP% indicates the trimethylpentane selectivity.
Triflic acid does not appear in the effluent.

EXAMPLE 8

11 cc of catalyst prepared in accordance with Example 3 are placed in a reactor of diameter 0.76 cm and length 26 cm.

A mixture containing isobutane as substrate and 1-butene as alkylating agent in an isobutane: 1-butene ratio of 20:1 is fed to the reactor at a temperature of 25° C., a pressure of 24 bar and a flow rate of 0.6 ml/min. The results obtained are shown in the following table:

| $C_8$ yield % molar | Conversion | TMP % | Time (hours) |
| --- | --- | --- | --- |
| 89 | 99 | 66 | 1 |
| 95 | 98 | 60 | 3 |
| 95 | 98 | 66 | 6 |

TMP% indicates the trimethylpentane selectivity.
Triflic acid does not appear in the effluent.

EXAMPLE 9

10 cc of catalyst prepared in accordance with Example 4 are placed in a reactor of diameter 0.76 cm and length 26 cm.

A mixture containing isobutane as substrate and 1-butene as alkylating agent in an isobutane: 1-butene ratio of 20:1 is fed to the reactor at a temperature of 25° C., a pressure of 24 bar and a flow rate of 0.6 ml/min. The results obtained are shown in the following table:

| $C_8$ yield % molar | Conversion | TMP % | Time (hours) |
| --- | --- | --- | --- |
| 78 | 98 | 86 | 0.5 |
| 95 | 96 | 86 | 2 |
| 98 | 98 | 84 | 5 |

TMP% indicates the trimethylpentane selectivity.
No emergence of triflic acid is observed within a period of 5 hours.

EXAMPLE 10

2.2 cc of catalyst prepared in accordance with Example 5 are placed in a reactor of diameter 0.76 cm and length 26 cm.
A mixture containing isobutane as substrate and 1-butene as alkylating agent in an isobutane: 1-butene ratio of 20:1 is fed to the reactor at a temperature of 25° C., a pressure of 20 bar and a flow rate of 0.11 ml/min. The results obtained are shown in the following table:

| $C_8$ yield % molar | Conversion | TMP % | Time (hours) |
|---|---|---|---|
| 95 | 99 | 79 | 0.25 |
| 98 | 99 | 66 | 1 |

TMP% indicates the trimethylpentane selectivity.

No emergence of triflic acid is observed within a period of one hour.

EXAMPLE 11 (Comparative)

The following example is conducted in accordance with the process described in EP433954, and shows that triflic acid adsorbed on silica is less active in an alkylation reaction than the catalyst of the present invention. 11 cc of 70–230 mesh silica are placed in a reactor of diameter 0.76 cm and length 26 cm, and heated for 2 hours in a dry nitrogen stream to 400° C. It is cooled under nitrogen, 1 ml of triflic acid are added and a mixture containing isobutane and 1-butene in an isobutane: 1-butene ratio of 20:1 is then fed to the reactor at a temperature of 25° C., a pressure of 17 bar and a flow rate of 0.9 ml/min. The results obtained are shown in the following table:

| $C_8$ yield % molar | Conversion | TMP % | Time (min) |
|---|---|---|---|
| 52 | 99 | 70 | 20 |
| 61 | 99 | 71 | 60 |
| 62 | 99 | 71 | 180 |

TMP% indicates the trimethylpentane selectivity.

Emergence of triflic acid is observed after 3 hours and 30 minutes. The observed elution time depends on the length of the silica bed. Elution is practically immediate if the triflic acid is distributed from the beginning over all the reactor silica.

We claim:

1. A catalyst consisting of silica, characterized in that the surface Si—OH groups of said silica are esterified with a fluoroalkylsulphonic acid of formula $CF_3(CF_2)_nSO_3H$, wherein n is a whole number between 0 and 11, said catalyst having:
    a) a Hammett acidity $Ho \leq -11.4$
    b) an IR signal at 1546 cm$^{-1}$ after treatment with pyridine.
2. A catalyst in accordance with claim 1, having a Hammett acidity $Ho < -12$.
3. A catalyst in accordance with claim 1, wherein the Si—OH groups are esterified by a fluoroalkylsulphonic acid of formula $CF_3(CF_2)_nSO_3H$, where n is a whole number between 0 and 5.
4. A catalyst in accordance with claim 3, wherein the fluoroalkylsulphonic acid is trifluoromethanesulphonic acid.
5. A catalyst in accordance with claim 4 having a Hammett acidity Ho of between −13.5 and −14.
6. A method for preparing a silica containing catalyst characterised in that the surface Si—OH groups of said silica are esterified with a fluoroalkylsulphonic acid of formula $CF_3(CF_2)_nSO_3H$, wherein n is a whole number between 0 and 11, said catalyst having a Hammett acidity $Ho < -11.4$ and an IR signal at 1546 cm$^{-1}$ after treatment with pyridine, consisting of the steps of:
    a) mixing together tetraethylorthosilicate and fluoroalkyl-sulphonic acid of formula $CF_3(CF_2)_nSO_3H$, wherein n is a whole number between 0 and 11, in aqueous solution in a $CF_3(CF_2)_nSO_3H/Si(OEt)_4$ weight ratio of between 0.001 and 0.3, to obtain a gel;
    b) drying the gel obtained;
    c) reacting the dried gel with thionyl chloride in a $SOCl_2$/gel weight ratio of between 100 and 1; and
    d) removing the excess thionyl chloride by distillation.
7. A method in accordance with claim 6, wherein in stage a) the $CF_3(CF_2)_nSO_3H/Si(OEt)_4$ weight ratio lies within the range of 0.05 and 0.2.
8. A method in accordance with claim 6, wherein stage a) is conducted at a temperature between ambient and 100° C. for a time of 0.5–24 hours.
9. A method in accordance with claim 6, wherein in stage b) the gel is dried under vacuum at a temperature of between 20° and 80° C. for 12–48 hours.
10. A method in accordance with claim 6, wherein stage c) is conducted at a temperature of between 20° and 50° C. for 4–12 hours.
11. A method in accordance with claim 6, wherein the distillation of stage d) is conducted under vacuum at ambient temperature.
12. A process for preparing a silica containing catalyst characterised in that the surface Si—OH groups of said silica are esterified with a fluoroalkylsulphonic acid of formula $CF_3(CF_2)_nSO_3H$, wherein n is a whole number between 0 and 11, said catalyst having a Hammett acidity $Ho < -11.4$ and an IR signal at 1546 cm$^{-1}$ after treatment with pyridine, consisting of thermally treating a fluoroalkylsulphonic acid of formula $CF_3(CF_2)_nSO_3H$, where n is a whole number between 0 and 11, and anhydrous silica in a $CF_3(CF_2)_nSO_3H/SiO_2$ weight ratio of between 0.001 and 0.3, at a temperature of between 50° and 300° C. for 12–48 hours.
13. A process in accordance with claim 12, wherein the temperature is between 100° and 200° C.
14. A process in accordance with claim 12, wherein the weight ratio of fluoroalkylsulphonic acid to anhydrous silica is between 0.05 and 0.2.
15. A process in accordance with claim 12, wherein the anhydrous silica is prepared by drying silica at a temperature of about 400° C. for 12–48 hours.
16. A process for preparing a silica containing catalyst characterised in that the surface Si—OH groups of said silica are esterified with a fluoroalkylsulphonic acid of formula $CF_3(CF_2)_nSO_3H$, wherein n is a whole number between 0 and 11, said catalyst having a Hammett acidity $Ho < -11.4$ and an IR signal at 1546 cm$^{-1}$ after treatment with pyridine, comprising the steps of: dissolving the fluoroalkylsulphonic acid $CF_3(CF_2)_nSO_3H$ in a solvent, mixing with anhydrous silica in a $CF_3(CF_2)_nSO_3H/SiO_2$ weight ration of between 0.001 and 0.3, removing the solvent under vacuum, and subsequently heating the resulting product at a temperature of between 50° and 300° C. for 12–48 hours.
17. A process in accordance with claim 16, wherein the solvent is selected from the group consisting of water, freons, trifluoroacetic acid and trifluoroacetic anhydride.
18. A process in accordance with claim 17, wherein the solvent is 1,1,2-trichloro-2,2,1-trifluoroethane.

* * * * *